United States Patent [19]

Zebehazy

[11] Plant 5,229

[45] May 8, 1984

[54] LEUCOTHOE PLANT—ZEBONARD VARIETY

[75] Inventor: Alex J. Zebehazy, Perry, Ohio

[73] Assignee: Conard-Pyle Company, West Grove, Pa.

[21] Appl. No.: 276,062

[22] Filed: Jun. 22, 1981

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Burns, Doane, Swecker & Mathis

[57] ABSTRACT

A new and distinct variety of Leucothoe is provided. While the new variety is believed to have originated as a cross-pollination of *Leucothoe fontanesiana* with pollen from *Leucothoe axillaris,* this cross cannot be confirmed. The new variety possesses smaller foliage which is less lanceolate than other varieties which are believed to have originated from the same cross.

1 Drawing Figure

SUMMARY OF THE INVENTION

My invention relates to a new, distinctive and useful form of Leucothoe plant which was originated by me at Perry, Ohio. A breeding program was carried out whereby plants of *Leucothoe fontanesiana* were pollinated with pollen from plants which were purchased as being *Leucothoe axillaris.* However, there is the possibility that the pollen parent may have actually been *Leucothoe fontanesiana* var. *nana.* Also, following the attempted pollen transfer, the flowers of the seed parent were not bagged thereby making possible the introduction of pollen from an unknown source.

The object of my breeding was to create a colorful new variety of Leucothoe which combined the hardiness of *Leucothoe fontanesiana* with the attractive dwarf growth habit of *Leucothoe axillaris,* and which exhibited improved foliage coloration and an improved plant habit over both parents. This objective was achieved, along with other improvements, and the new variety exhibits a combination of characteristics which distinguish it from all other forms of Leucothoe of which I am aware.

The following combination of characteristics is exhibited by the new variety:

(a) a dense, compact, symmetrical habit of growth which is much more attractive and compact than that of the *Leucothoe fontanesiana* parent, (b) highly unique winter coloration which ranges from deep green to a greenish bronze making the new variety an outstanding source of color in the landscape year-round, (c) outstanding tolerance to shade, making the new variety an important addition to that small group of plants that does well in reduced sunlight, (d) the substantial absence of dead branches which are commonly found with *Leucothoe fontanesiana,*

(e) increased tolerance to cold when compared to *Leucothoe axillaris,* as is evidenced by the fact that the new variety has survived temperatures of −15° F. with little to no damage, whereas *Leucothoe axillaris* is listed as hardy to 0° F., and (f) foliage which is considerably smaller and less lanceolate, as well as winter foliage which is considerably less glossy and of a darker coloration than that of the Zeblid variety (U.S. Ser. No. 161,870, filed June 23, 1980) of the same cross.

Asexual reproduction by cuttings of my new variety has been accomplished at Perry, Ohio, and at West Grove, Pa. Succeeding propagations have shown the unique combination of characteristics is fully established and is transmitted to successive generations.

The new variety has been named the Zebonard variety.

BRIEF DESCRIPTION OF THE PHOTOGRAPH

The accompanying photograph shows a typical specimen of my new variety of Leucothoe during late May as depicted in color as true as is reasonably possible to make the same in a color photograph of this character. The specimen shown in the photograph is a three year old plant growing in the ground at West Grove, Pa.

DETAILED DESCRIPTION

The following is a detailed description of my new variety made from the observation of three year old plants growing in the ground at West Grove, Pa. Color terminology is in accordance with the R.H.S. Colour Chart of The Royal Horticultural Society, London, England.

Parentage:

*Leucothoe fontanesiana* × *Leucothoe axillaris.*

Foliage:

*Type.*—Evergreen. Leaves lanceolate to ovate. The leaves are more ovate than those of the Zeblid variety (U.S. Ser. No. 161,870, filed June 23, 1980) and the Zebekot variety (U.S. Ser. No. 276,061, filed concurrently herewith) of the same cross. Apex slightly acuminate, base obtuse, margins serrulate.

*Size of mature leaves.*—From approximately 4.1 to 7.5 cm. in length, with an average of approximately 5.7 cm.; from approximately 2.1 to 3.6 cm. in width, with an average of approximately 2.8 cm. Petiole length from approximately 0.6 to 1.0 cm. Internode length from approximately 1.5 to 2.1 cm.

*Color.*—Fully expanded immature leaves in May, upper surface — slightly darker than Yellow-Green Group 144A; under surface — slightly lighter than Yellow-Green Group 146C. The immature leaves have a slight crimson cast throughout the leaf. Mature leaves in May, upper surface — Yellow-Green Group 147A; under surface — closest to Yellow-Green Group 146C. Leaves in March — from Greyed-Purple Group 187A to 187C, with green tones; Young shoots in May — slightly yellower than Green Group 143B to 143C. Petiole color in May — Red-Purple Group 60A.

Rate of growth: Average height and breadth of mature two year old plants is approximately 10 inches and approximately 15 inches, respectively.

Flowers: The flowers and racemes of the present variety appear in May and more closely resemble those of *Leucothoe axillaris* than those of *Leucothoe fontanesiana.* The raceme length for the new variety commonly averages approximately 1.5 to 2.5 cm., and the raceme length for *Leucothoe fontanesiana* is often twice this length. The individual flowers of the new variety are ovate in shape, have an average length of approximately 5 to 6 mm., have an average base width of approximately 3 to 4 mm., and have an average apex width of approximately 3 mm. or less.

I claim:

1. A new and distinct variety of Leucothoe substantially as herein shown and described, characterized particularly as to novelty by the unique combination of:

(a) a dense, compact, symmetrical habit of growth which is much more attractive and compact than that of the *Leucothoe fontanesiana* parent, (b) highly unique winter coloration which ranges from green to a greenish bronze making the new variety an outstanding source of color in the landscape year-round, (c) outstanding tolerance to shade, making the new variety an important addition to that small group of plants that does well in reduced sunlight, (d) the substantial absence of dead branches which are commonly found with *Leucothoe fontanesiana,*

(e) increased tolerance to cold when compared to *Leucothoe axillaris,* as is evidenced by the fact that the new variety has survived temperatures of −15° F. with little to no damage, whereas *Leucothoe axillaris* is listed as hardy to 0° F., and (f) foliage which is considerably smaller and less lanceolate, as well as winter foliage which is considerably less glossy and of a darker coloration than that of the Zeblid variety of the same cross.

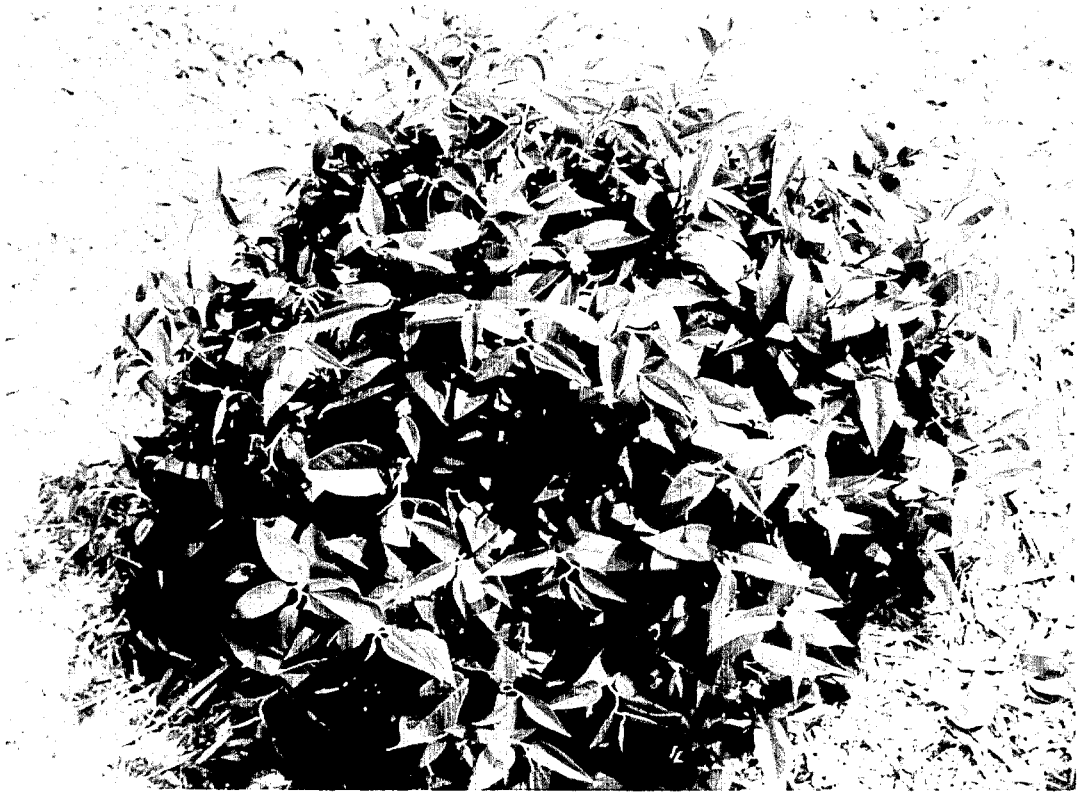

* * * * *